(12) United States Patent
Spenciner (10) Patent No.: US 11,717,394 B2
(45) Date of Patent: Aug. 8, 2023

(54) FLIPPING-TYPE GRAFT FIXATION DEVICE AND METHOD WITH LOW FLIPPING DISTANCE

(71) Applicant: DEPUY SYNTHES PRODUCTS, LLC, Raynham, MA (US)

(72) Inventor: David B. Spenciner, North Attleboro, MA (US)

(73) Assignee: DEPUY SYNTHES PRODUCTS, INC, Raynham, MA (US)

( * ) Notice: Subject to any disclaimer, the term of this patent is extended or adjusted under 35 U.S.C. 154(b) by 451 days.

(21) Appl. No.: 17/079,711

(22) Filed: Oct. 26, 2020

(65) Prior Publication Data

US 2021/0038365 A1 Feb. 11, 2021

Related U.S. Application Data

(62) Division of application No. 14/041,764, filed on Sep. 30, 2013, now Pat. No. 10,813,741.

(51) Int. Cl.
*A61F 2/08* (2006.01)

(52) U.S. Cl.
CPC ..... *A61F 2/0811* (2013.01); *A61F 2002/0823* (2013.01); *A61F 2002/0852* (2013.01); *A61F 2002/0882* (2013.01)

(58) Field of Classification Search
CPC ........ A61B 17/0401; A61B 2017/0404; A61B 2017/0414; A61B 2017/0417; A61F 2/0811; A61F 2002/0817; A61F 2002/0823; A61F 2002/0847; A61F 2002/0852; A61F 2002/0882
See application file for complete search history.

(56) References Cited

U.S. PATENT DOCUMENTS

| | | | |
|---|---|---|---|
| 5,306,301 | A | 4/1994 | Graf |
| 5,645,588 | A | 7/1997 | Graf |
| 5,769,894 | A | 6/1998 | Ferragamo |
| 6,086,591 | A | 7/2000 | Bojarski |
| 6,193,754 | B1 * | 2/2001 | Seedhom ............... A61F 2/08 623/13.11 |
| 6,352,603 | B1 | 3/2002 | Bryant |
| 6,902,573 | B2 | 6/2005 | Strobel |
| 7,566,339 | B2 | 7/2009 | Fallin |
| 7,594,923 | B2 | 9/2009 | Fallin |
| 7,806,909 | B2 | 10/2010 | Fallin |
| 8,545,558 | B2 | 10/2013 | Spenciner |

(Continued)

FOREIGN PATENT DOCUMENTS

| | | |
|---|---|---|
| CN | 103251463 A | 8/2013 |
| CN | 103826568 | 5/2014 |

(Continued)

*Primary Examiner* — Darwin P Erezo
*Assistant Examiner* — Christian D Knauss (57) ABSTRACT

A graft retention device has an elongated body with first and a second ends, and a midpoint therebetween. A pair of elongated slots through the body defines a tang therebetween. At least one of the slots have an open first end into the body at the body first end such that the first end is closed via a retention line between the tang and the body. A graft retention loop disposed over the tang is slidable therealong from a first position closer to the body first end and a second position closer to the midpoint.

12 Claims, 5 Drawing Sheets

(56) References Cited

U.S. PATENT DOCUMENTS

| | | | |
|---|---|---|---|
| 2002/0173788 A1* | 11/2002 | Bojarski | A61B 17/0401 606/60 |
| 2007/0233241 A1* | 10/2007 | Graf | A61B 17/0401 623/13.14 |
| 2007/0270857 A1* | 11/2007 | Lombardo | A61B 17/0401 623/13.12 |
| 2009/0234396 A1 | 9/2009 | Medoff | |
| 2010/0305585 A1 | 12/2010 | Fallin | |
| 2010/0318126 A1 | 12/2010 | Fallin | |
| 2013/0085526 A1* | 4/2013 | Graf | A61F 2/0811 606/232 |
| 2013/0085527 A1* | 4/2013 | Ferragamo | A61F 2/0811 606/232 |
| 2013/0116787 A1 | 5/2013 | Ferragamo | |
| 2013/0204366 A1 | 8/2013 | Spenciner | |
| 2014/0018917 A1 | 1/2014 | Spenciner | |

FOREIGN PATENT DOCUMENTS

| | | |
|---|---|---|
| EP | 2191791 A2 | 6/2010 |
| EP | 2623066 | 8/2013 |
| FR | 2926456 A1 | 7/2009 |
| GB | 2288739 A | 11/1995 |
| JP | 2001-510364 | 7/2001 |
| JP | 2013-158649 | 8/2013 |
| WO | WO 2007109665 A1 | 9/2007 |
| WO | WO 2013049445 A1 | 4/2013 |
| WO | WO 2013049453 A1 | 4/2013 |

\* cited by examiner

FLIPPING-TYPE GRAFT FIXATION DEVICE AND METHOD WITH LOW FLIPPING DISTANCE

RELATED APPLICATIONS

This application is a divisional of U.S. patent Ser. No. 14/041,764, filed Sep. 30, 2013, now U.S. Pat. No. 10,813,741. The complete disclosure of the aformentioned related U.S. patent application is hereby incorporated herein by reference for all purposes.

BACKGROUND

This application relates to graft fixation, and more particularly to graft tissue fixation employing flipping-type fixation devices.

Flipping-type fixation devices, such as disclosed in U.S. Pat. Nos. 5,306,301 and 5,645,588 which are incorporated herein by reference, allow a simple procedure to be used for fixing tissue such as in an Anterior Cruciate Ligament (ACL) reconstruction. Such device comprises an elongated bar having a central suture loop depending therefrom. A tunnel is prepared in the femur from a position at or near the patellar surface up through a portion of the femur and exiting through the side of the femur at a superior location. A graft is looped over the loop attached to the elongated bar. The bar is able to pass in one direction up through the tunnel. After exiting the superior end of the tunnel, the bar is flipped approximately 90 degrees so that it will not pass back through the tunnel and is positioned against the femur with the loop and graft hanging down into the tunnel therefrom. Tension on the graft keeps the bar in place against the bone surface.

To initiate the flipping, however, the bar must be passed completely outside of the tunnel. When it is then placed down against the bone the suture loop falls back into the tunnel by the amount that it was pulled free of the tunnel, about 50% of the length of the bar. This decreases the contact of the graft with the bone in the tunnel. Also, longer loop lengths have the potential to increase motion of the graft within the tunnel, thus potentially slowing the healing process in which the graft attaches to the bone.

U.S. Patent Publication No. 20130204366, incorporated herein by reference, provides a bar in which the graft retention loop is able to move axially along the bar thereby reducing the distance the graft is pulled out of the tunnel during the flipping procedure.

SUMMARY OF THE INVENTION

A graft retention device according to the present invention comprises an elongated body having a first end and a second end, a midpoint therebetween, and an upper surface and a lower surface. A first elongated slot and a second elongated slot through the body from the upper surface to the lower surface define tang therebetween. At least one of the first and second slots have an open first end into the body at the body first end such that the first end is closed via a retention line between the tang and the body. A graft retention loop disposed over the tang is slidable therealong from a first position closer to the body first end and a second position closer to the midpoint.

Preferably, each of the first slot and second slot has an open first end and each has a separate retention line or a single retention line which encloses both the first slot and the second slot.

Preferably, at least a portion of the retention line extends longitudinally beyond the first end of the body.

In one aspect of the invention, the retention line comprises a flexible material. The retention line can comprise an elastic material. The retention line can comprise a metal wire.

Preferably, a leading line connects to the body at the second end.

Preferably, the tang slopes downwardly away from the first end.

Preferably, the graft retention device is provided in a sterile condition.

Preferably, the second position is located near the midpoint such as within a central 25% of a length of the elongated body between its first end and its second end.

In one aspect of the invention, a trailing line connects to the body adjacent the slots and extends therefrom, when the graft retention loop is in the first position, through the graft retention loop toward the first end such that tension applied to the trailing line will thus tend to urge the graft retention loop away from the first position and toward the second position.

A method according to the present invention provides for fixing a graft ligament into a bone tunnel. The method comprises the steps of: a) forming a graft construct by disposing the graft ligament over a loop slidably disposed upon a tang formed between two elongated slots of an elongated fixation buckle, the loop being slidable along the tang from a first position nearer a first end of the buckle to a second position nearer a midpoint of the buckle; b) pulling the graft construct up through the bone tunnel with a second end of the buckle leading and the loop in the first position; c) retaining the loop in the slots and on the tang in the first position via a retention line between the tang and a body forming the buckle at the first end of the buckle; and d) after the buckle has been pulled through the tunnel, reorienting the buckle to be crosswise to the tunnel on the bone adjacent the tunnel with the loop depending into the tunnel from the second position on the buckle.

Preferably, a portion of the retention line extends longitudinally beyond the first end of the buckle body when the loop is in the first position. Preferably, the graft is moved no further upwards during the performance of step c) from its final position after step d) than 3.5 mm. More preferably, the graft is moved no further upwards during the performance of step c) than its final position after step d). Most preferably, the bone tunnel comprises a lower graft channel and an upper passing channel, with the graft channel having a width exceeding a maximum width of the passing channel thereby forming an end surface of the graft channel where it meets the passing channel and wherein the method further comprises the step of holding the graft in compression against the end surface of the graft channel after step d).

DETAILED DESCRIPTION

Figure 1:
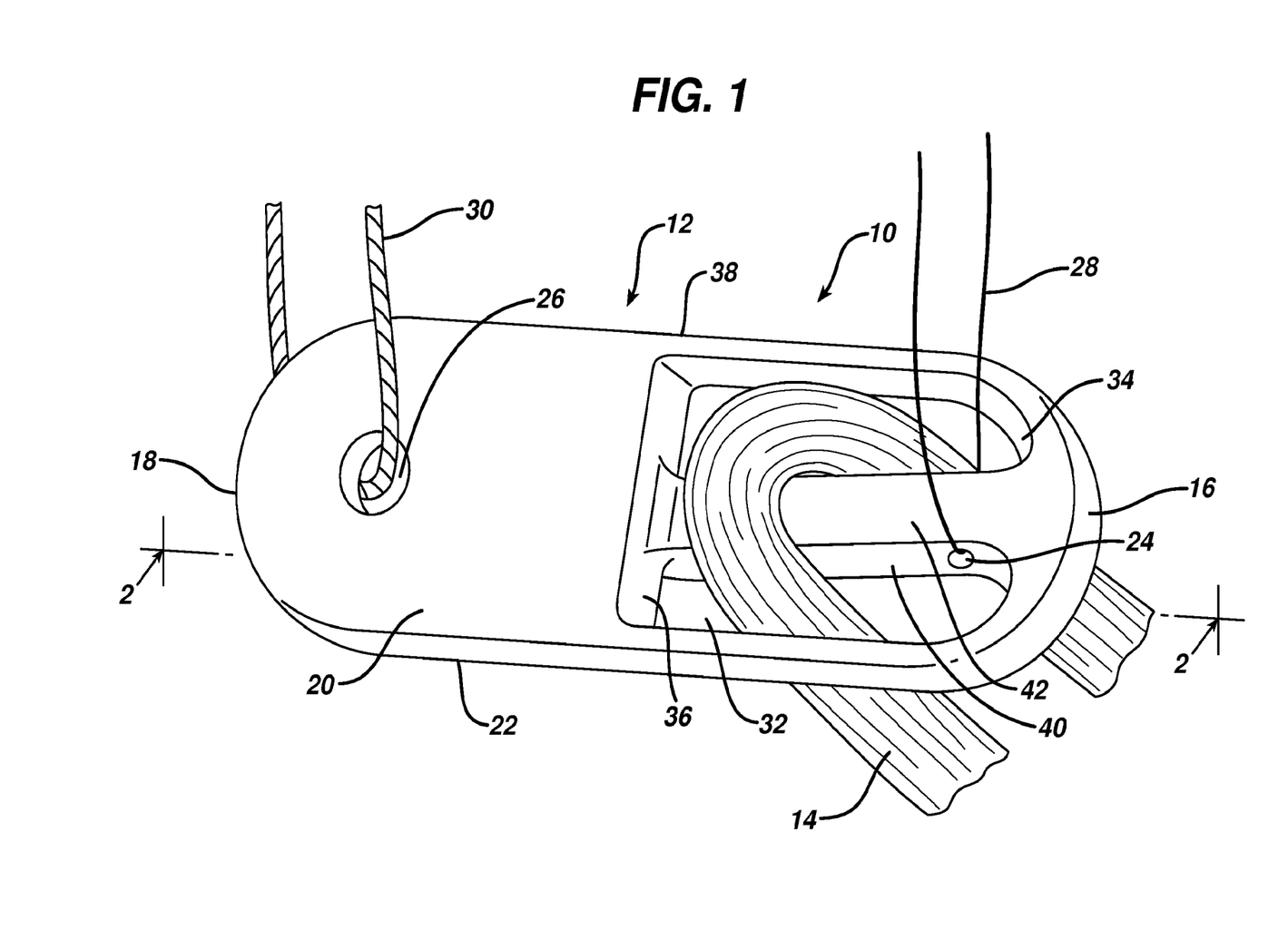
FIG. 1 is a perspective view of a fixation device buckle according to the present invention.
Figure 2:
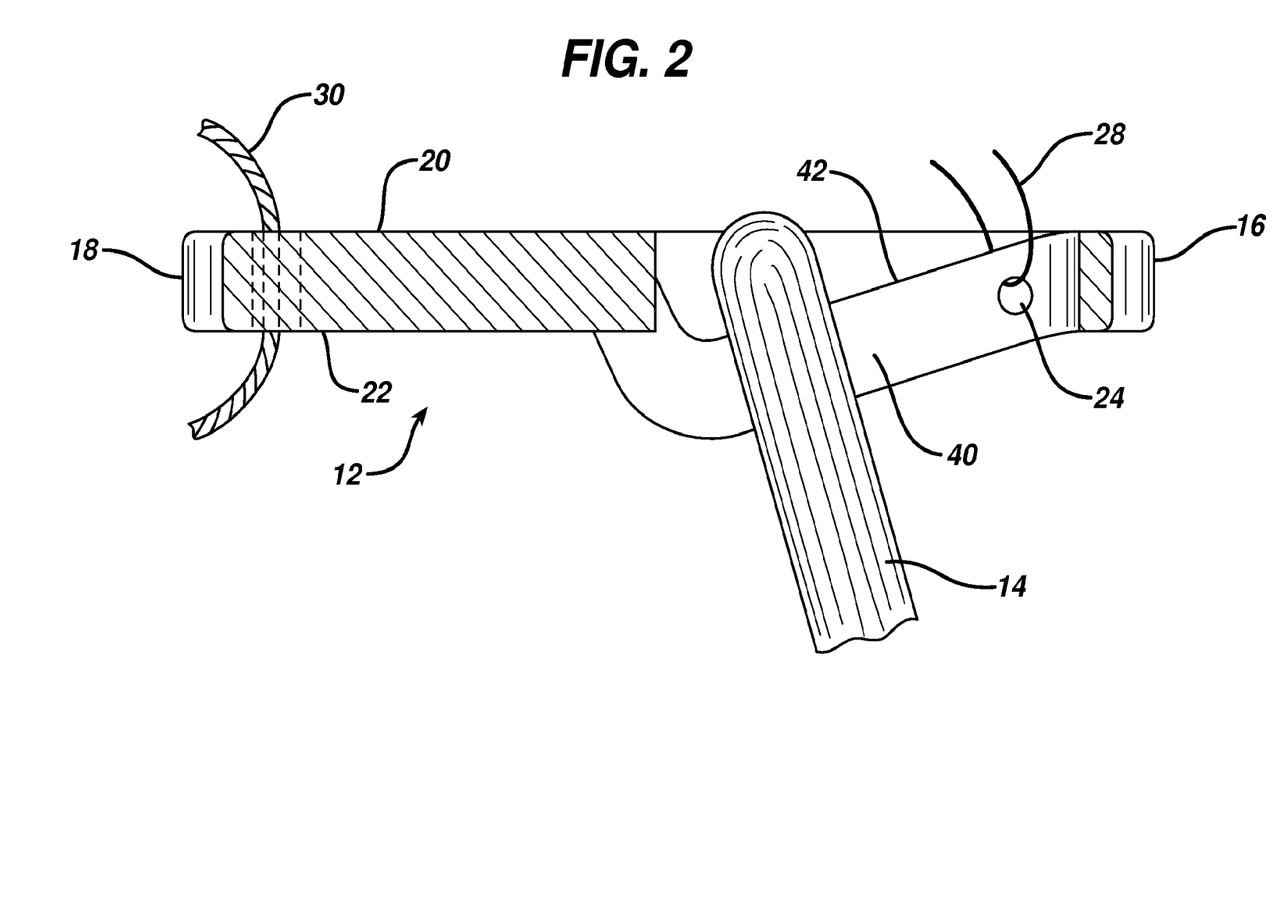
FIG. 2 is a sectional view taken along line 2-2 of FIG. 1.

FIGS. 1 and 2 show a graft fixation device 10 according to the present invention. It comprises an elongated bar or buckle 12 having a graft receiving loop 14 depending therefrom. The buckle 12 comprises a first end 16 and second end 18, and an upper surface 20 and lower surface 22. The terms "upper" and "lower" and related terms such as "upwards" are used herein with reference to the surfaces of the buckle 12 just defined, with the lower surface 22 being that surface which will face a bone (not shown in FIG. 1) when the buckle 12 is employed.)

A pair of longitudinal slots 32 penetrates the buckle 12 from the upper surface 20 to the lower surface 22 and extends from a first end 34 adjacent the buckle first end 16 to a second end 36 at a midpoint 38 of the buckle 12. The slots 32 define a retention tang 40 therebetween. An upper surface 42 of the retention tang slopes downwardly from the first end 34 of the slots 32 to the second end 36 to encourage the loop 14 to migrate toward the midpoint 38 at implantation. The loop 14 is received through the slots 32 and slides along the retention tang upper surface 42.

A first hole 24 penetrates the tang 40 laterally adjacent the first end 16 and a second hole 26 penetrates the buckle 12 at the second end 18, passing from the upper surface 20 to the lower surface 22. The first hole 24 receives a trailing line 28 and the second hole 26 a leading line 30 for guiding the buckle 12 during implantation. As best seen in FIG. 2, when the loop 14 is toward the first end 34 it overlaps the first hole 24. When the trailing line 28 is tightened upwardly during the flipping portion of implantation it will tend to push the loop 14 away from the first end 34. Placement of the hole 24 inboard of the first end 34 also allows the first end 34 of the slots 32 to be closer to the first end 16 of the buckle 12 and thereby reduce the flipping distance.

The trailing line 28 and leading line 30 are preferably formed of ORTHOCORD #2 suture available from Ethicon, Inc. of Somerville, N.J. The leading line 30 may experience higher stress than the trailing line 28 while placing the fixation device 10 as will become apparent as the placement procedure is described. The second hole 26 is shown slightly larger than the first hole 24 (although they could be made the same size) and the leading line 30 can be a higher strength suture such as with a larger diameter than the trailing line 28. This difference can be used to differentiate the leading line 30 and trailing line 28. They can also be differentiated in some other fashion such as via varying colors or visual patterns.

Preferably, the vertical dimension of the retention tang 40 remains constant from the first end 34 to second end 36 to enhance its strength and rigidity, with the retention tang 40 thus depending slightly below the buckle lower surface 22 at the midpoint 38. The tang 40 is shown with a slope below the upper surface 20 of 13.6 degrees but could be anywhere from zero to about 45 degrees. It could also vary in slope, such as getting progressively steeper toward the midpoint 38 to encourage the loop to stay at the midpoint 38 after implantation.

Preferably, for an ACL repair the buckle 12 is approximately 12 mm long, 4 mm wide and 1.5 to 2.5 mm thick, with the thickest portion being the midpoint 38 where the tang 40 depends. The tang 40 is approximately 1.5 mm thick. The buckle 12 is preferably formed of a biocompatible material such as 6Al-4V Ti alloy. Preferably, the loop 14 is woven of ultra-high molecular weight polyethylene, such as DYNEEMA, and polyester. The material of the loop 14 is preferably about 2 mm in diameter, preferably being in a range of from #2-0 up through about 4 mm, and the loop 14 is preferably between about 8 mm and 60 mm long. The loop 14 can be woven onto the buckle 12 to form a continuous loop without knots. U.S. Pat. No. 6,352,603 to Bryant, incorporated herein by reference, illustrates one method for achieving such a construct.

Figure 3:
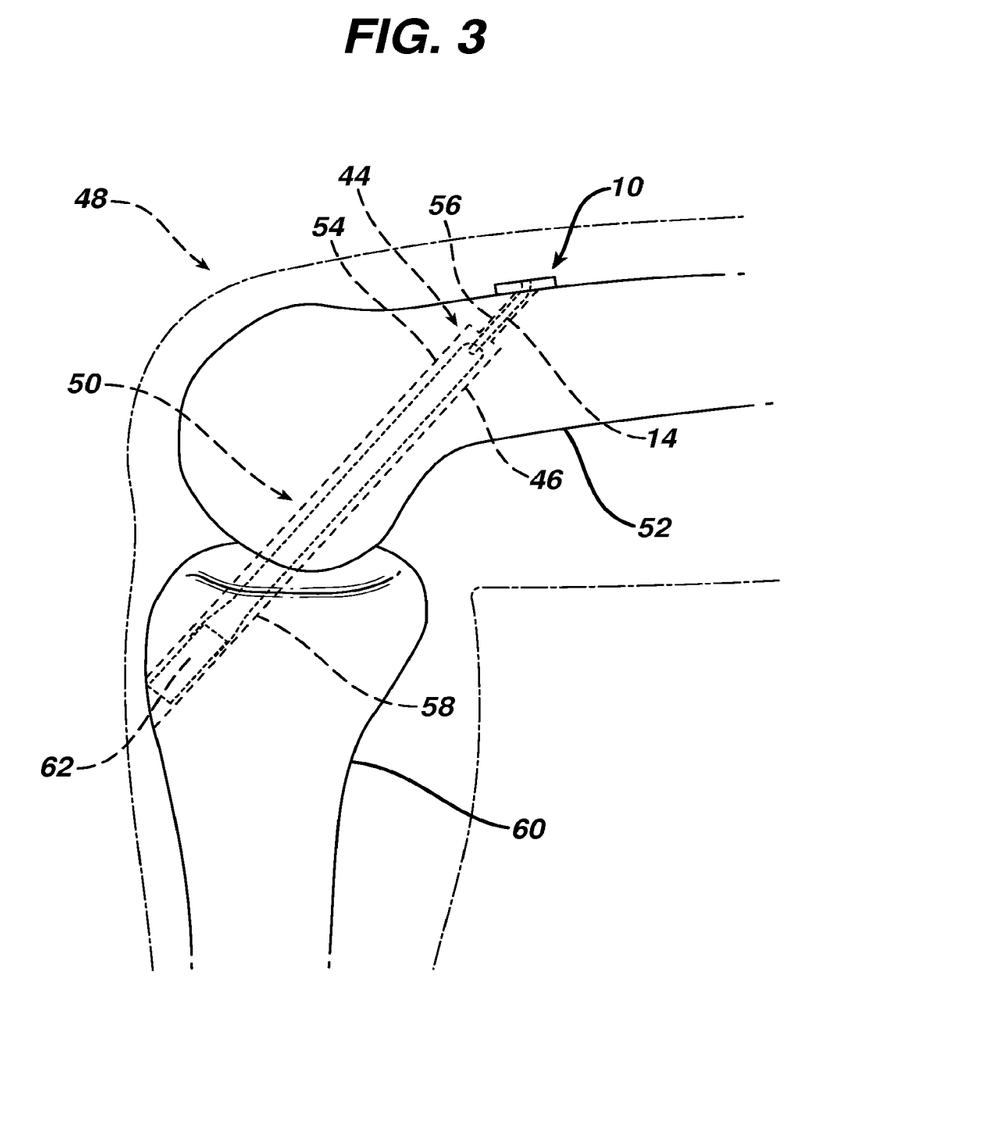
FIG. 3 is a side elevation view in cross-section of a ACL repair in a knee employing the fixation device of FIG. 1.

Turning also now to FIG. 3, a graft construct 44 comprises a tissue graft 46 looped over the loop 14 of the fixation device 10 and is show in place in a patient's leg 48. A tunnel 50 in the leg's femur 52 comprises a larger diameter inferior portion or socket 54 sized to accommodate the graft 46 and a smaller diameter superior portion or passing channel 56 sized to accept the buckle 12 in a lengthwise orientation. The buckle 12 sits against the femur 52 in a sideways orientation with the loop 14 depending down through the passing channel 56 and into the socket 54 in which is placed the graft 46. An opposite end of the graft 46 is placed into a tibial tunnel 58 in the leg's tibia 60 and held in place with an anchor 62 such as the INTRAFIX® anchor available from DePuy Mitek Inc. of Raynham, Mass.

Figure 4A:
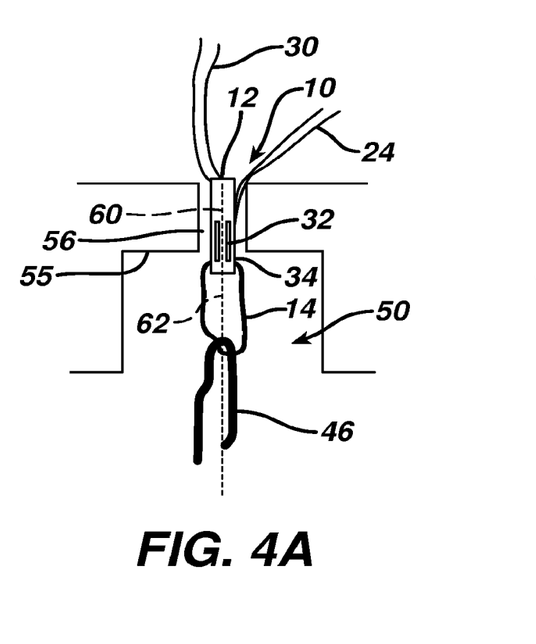
FIGS. 4A to 4D are side elevation views in cross-section of an ACL repair procedure employing the fixation device of FIG. 1.
Figure 4B:
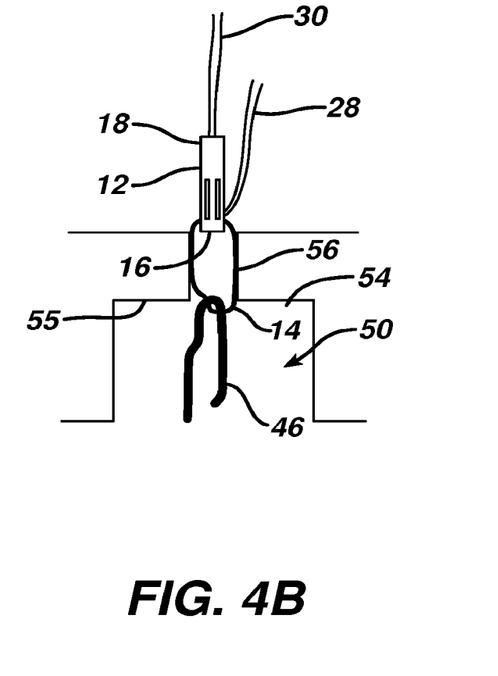

Turning also now to FIGS. 4A to 4D the process of passing the buckle 12 up through the tunnel 50 and especially the passing channel 56 will be described. At the start of the procedure, the graft tissue 46 is threaded through the loop 14. A longitudinal axis 60 of the buckle 12 is oriented coaxially with a longitudinal axis 62 of the tunnel 50, with the loop 14 depending from the first end 34 of the slots 32 (FIG. 4A). Tension on the leading line 30 pulls the second end 18 of the buckle 12 upwardly out of the passing channel 56 until the first end 16 is free of the passing channel 56 (FIG. 4B). Preferably, the loop 14 and the passing channel 56 are dimensioned so that if the graft construct 44 is pulled up until the graft tissue 46 abuts an end 55 of the socket 54 the first end 16 of the buckle 12 has just cleared the end of the passing channel 56 thus providing tactile feedback to the surgeon that the buckle 12 is properly positioned to be rotated. The graft 46 shown in FIGS. 4A to 4D is not to scale and is shown as a thin line so as to better illustrate the construction of the socket 54. In reality the graft 46 would be fatter such that it entirely fills the width of the socket 54. Contact between the graft 46 and the bone forming the socket 54 allows the graft to grow into and merge with the bone to form a permanent repair.

Figure 4C:
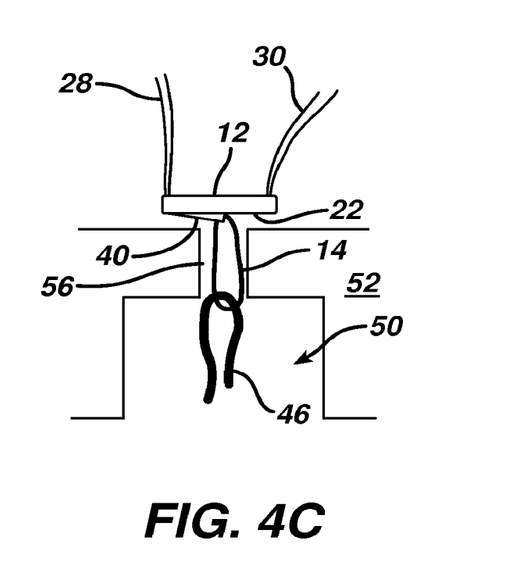
Figure 4D:
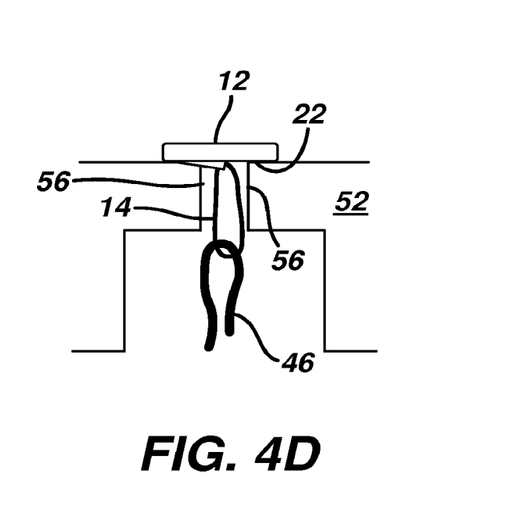

Rotation is approximately 90 degrees and can occur by applying tension to the trailing line 28 (FIG. 4C). The final orientation depends upon the angle at which the tunnel 50 penetrates the femur 52. As the buckle 12 is rotated, opposing tension supplied by the graft tissue 46 tends to cause the loop 14 to slide along the retention tang 40 leaving it depending down into the passing channel 56 from the midpoint 38 of the buckle 12. This occurs with a distinct snapping motion that can be felt by the surgeon through the trailing line 28 to provide tactile feedback that the migration has occurred properly. The trailing line 28 and leading line 30 are then removed and tension from the graft tissue 46 pulls the buckle 12 lower surface 22 firmly against the femur 52 (FIG. 4D). The crosswise orientation of the buckle 12 versus the passing channel 56 and the loop 14 depending from the midpoint 38 of the buckle 12 prevent the buckle from migrating back into the passing channel 56 thus providing secure fixation of the graft tissue 46.

The slope of the tang upper surface 42 assists in urging the loop 14 toward the midpoint 38. Its angle on the femur 52 versus the tunnel 50 also tends to pull the loop 14 across the buckle 12 to sit at the slot second ends 36 and the buckle 12. Locating the ends 36 at the midpoint 38 thus helps keep the loop 14 seated at the midpoint 38. In terms of final seating of the loop 14 the term "midpoint" can be broadly construed. Seating at the exact middle of the buckle 12 provides an equal amount of buckle to each side thereof to minimize any chance that the buckle 12 can slip along the bone in such a fashion that and end thereof could fall back into the passing channel 56. In practical terms the loop 14 can be seated in other locations yet still be safely situated to prevent the buckle 12 from falling back into the passing channel 56. Preferably, the loop 14 is seated somewhere in the middle 50% of the length of the buckle 12 and more preferably within the middle 25%.

The flipping distance is representative of the gap between the graft 46 and the end of the socket 54. Ideally this gap is zero and the graft 46 extends all the way to the end of the socket 54.

Figure 5:
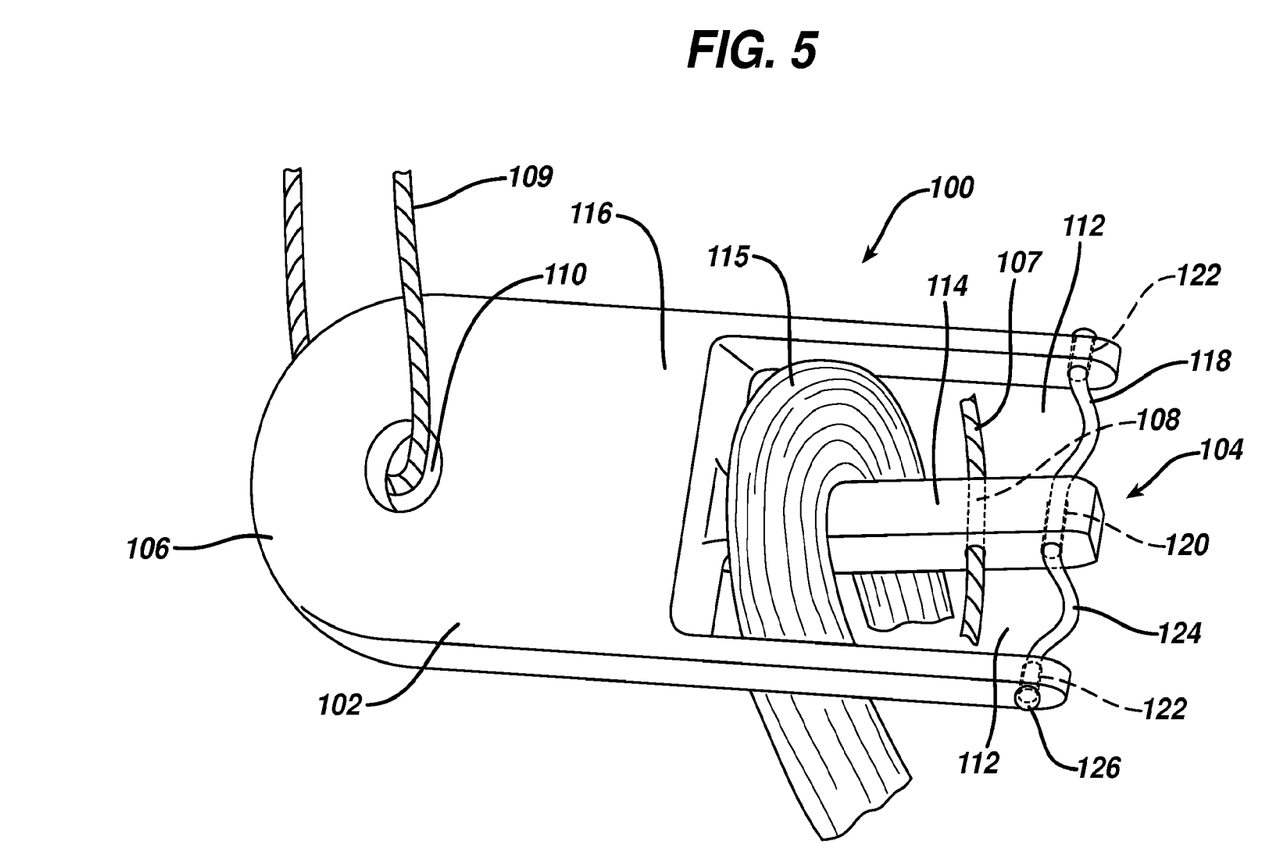
FIG. 5 is a top perspective view of an alternative embodiment of a buckle according to the present invention.

FIG. 5 illustrates a further embodiment of a buckle 100 according to the present invention. It comprises a body 102 having first and second ends 104 and 106 with holes 108 and 110 for trailing and leading lines 107 and 109 respectively. It also has slots 112 forming a tang 114 for supporting a graft support loop 115. The slots 112 extend from a midpoint 116 to the first end 104 rather than being enclosed by the body 102 at the first end 104 as in the previous embodiment. To retain the loop on the tang 114 a retaining line 118 is provided through aperture 120 in the tang 114 and adjacent apertures 122 in the body 102.

The retaining line 118 can be a suture, wire or other material with sufficient tensile strength to retain the loop. It can be flexible, stretchable or rigid. As shown in FIG. 5 it bows outwardly 124 between the tang 114 and adjacent body 102 to further minimize the flipping distance, but it could be made straight with no bowing. The bowing 124 can be present in a resting state such as being formed in a wire, or may by dynamically formed under force of the loop 115 against the retaining line 118 if the line 118 is formed of an elastic material which stretches to form the bowing 124. For instance the line 118 could be formed of a suture with a lower than average modulus of elasticity such as PDS (Polydioxanone) or Prolene and multiple lengths of such suture could be employed to form the line 118 with sufficient strength. Rubber or silicone materials, as for instance silicone tubing, of an implantable grade could are other possibilities for an elastic material. The bowing 124 could be formed by the line 118 being flexible, such as a suture, with sufficient slack as to form the bowing 124 especially when the loop presses against it.

Fixation of the line 118 in the apertures 122 can be effected by providing knots 126 the ends of the line 118, particularly if it is formed of suture, such that the knots 126 cannot pass through the apertures 122. Other methods for fixation include welding, adhesives, interference screws etc.

With sufficient bowing 124 the buckle 100 could have a flipping distance of zero or even a negative value allowing the graft to be seated to the end 55 of the graft socket 54 (not shown in FIG. 5). With sufficient bowing 124 and a negative flipping distance, the graft will reach the end 55 of the graft socket 54 as the buckle 100 is flipped. After the flipping is completed and the buckle 100 is seated against the bone the loop 115 would be pulled upwards versus its position during flipping such that a tension in the loop 115 would pull the graft into contact with the end 55 of the socket 54 with a contact force thereagainst thereby maximizing the bone to graft contact area of the completed repair. In prior devices this bone surface 55 is wasted as they do not allow the graft to contact it sufficient to achieve ingrowth between the graft and the bone.

The loop 115 is preferably a continuous closed loop. Formation of such a structure through weaving etc. is made more difficult if it must be formed around the tang 114. With the design of FIG. 5 the loop 115 can be formed alone which is much easier and then slipped onto the tang 114 prior to placing the line 118 onto the buckle 100. This simplifies manufacturing.

Refinements and variations to the buckle could include slots which extend to both sides such that the second side mirrors the first, and the retention tang sloping down from both ends toward the center. This would allow a surgeon to pull the buckle up through the tunnel 50 by either end. Also, the upper surface of the retention tang could be rounded to provide a better surface for the loop 14 to ride over and lessen chafing of the loop 14.

Provision can be made to discourage the loop 14 from moving away from the midpoint 38, such as by providing barbs (not shown) along the upper surface 42 or other areas of the buckle 12 where they may engage the loop 14 as it slides along the slots 32. The tang can have a pronounced dip to capture and retain the loop 14 at the midpoint.

The buckle is particularly suited to ACL repair, but can be useful in other repairs such as for example reattachment of a biceps brachii tendon.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A graft retention device comprising:
    an elongated body having a first end and a second end, a midpoint therebetween, and an upper surface and a lower surface;
    a first elongated slot and a second elongated slot through the body from the upper surface to the lower surface, defining a tang therebetween;
    at least one of the first slot and the second slot having an open slot first end into the body at the body first end, such open slot first end being closed via a retention line between the tang and the body; and
    a graft retention loop disposed over the tang and slidable therealong from a first position closer to the body first end and a second position closer to the midpoint.

2. A graft retention device according to claim 1 wherein each of the first slot and second slot has an open first end and each has a separate retention line.

3. A graft retention device according to claim 1 wherein each of the first slot and second slot has an open first end and wherein a single retention line encloses both the first slot and the second slot.

4. A graft retention device according to claim 1 wherein at least a portion of the retention line extends longitudinally beyond the first end of the body.

5. A graft retention device according to claim 1 wherein the retention line comprises a flexible material.

6. A graft retention device according to claim 1 wherein the retention line comprises an elastic material.

7. A graft retention device according to claim 1 wherein the retention line comprises a metal wire.

8. A graft retention device according to claim 1 and further comprising a leading line connected to the body at the second end.

9. A graft retention device according to claim 1 wherein the tang slopes downwardly away from the first end.

10. A graft retention device according to claim 1 which is sterile.

11. A graft retention device according to claim 1 wherein the second position is located within a central 25% of a length of the elongated body between its first end and its second end.

12. A graft retention device according to claim 1 and further comprising a trailing line connected to the body adjacent the slots and extending therefrom, when the graft retention loop is in the first position, through the graft retention loop toward the first end such that tension applied to the trailing line will thus tend to urge the graft retention loop away from the first position and toward the second position.

* * * * *